(12) United States Patent
Chen

(10) Patent No.: US 11,524,105 B1
(45) Date of Patent: Dec. 13, 2022

(54) NASAL ASPIRATOR CAPABLE OF EFFECTIVELY PREVENTING BACKFLOW AND CONTROL METHOD THEREOF

(71) Applicant: Hetaida Technology Co., Ltd., Dongguan (CN)

(72) Inventor: Zhenguang Chen, Dongguan (CN)

(73) Assignee: HETAIDA TECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 17/685,389

(22) Filed: Mar. 3, 2022

(51) Int. Cl.
*A61M 1/00* (2006.01)

(52) U.S. Cl.
CPC .............. *A61M 1/682* (2021.05); *A61M 1/65* (2021.05); *A61M 2210/0618* (2013.01)

(58) Field of Classification Search
CPC .................. A61M 1/682; A61M 1/65; A61M 2210/0618; A61M 1/0003
See application file for complete search history.

(56) References Cited

U.S. PATENT DOCUMENTS

| | | | | |
|---|---|---|---|---|
| 3,768,478 A | * | 10/1973 | Fertik | A61M 1/784 604/320 |
| 5,599,302 A | * | 2/1997 | Lilley | F41B 11/642 604/500 |
| 2002/0198488 A1 | * | 12/2002 | Yao | A61M 1/0062 604/35 |
| 2003/0225427 A1 | * | 12/2003 | Chen | A61M 1/0058 606/162 |
| 2008/0312674 A1 | * | 12/2008 | Chen | A61M 1/0058 606/162 |
| 2009/0048581 A1 | * | 2/2009 | Sebban | A61M 1/0003 604/319 |
| 2016/0045698 A1 | * | 2/2016 | Chaturvedi | A61M 16/0479 128/204.21 |

* cited by examiner

*Primary Examiner* — Nilay J Shah
(74) *Attorney, Agent, or Firm* — Leong C. Lei

(57) ABSTRACT

A nasal aspirator capable of effectively preventing backflow and a control method thereof are disclosed. The nasal aspirator includes a casing, a control board, a lower suction nozzle, an upper suction nozzle, a liquid storage cup, and an air pump unit. The control board is disposed in the casing. The lower suction nozzle is disposed on an upper end of the casing. The lower suction nozzle has a chamber and a suction passageway therein. The chamber has an opening facing upward. An upper end of the suction passageway communicates with the chamber. A detection system for detecting a liquid is provided in the chamber. The detection system is connected to the control board.

9 Claims, 5 Drawing Sheets

NASAL ASPIRATOR CAPABLE OF EFFECTIVELY PREVENTING BACKFLOW AND CONTROL METHOD THEREOF

BACKGROUND OF THE INVENTION

1. Field of the Invention

The present invention relates to a nasal aspirator, and more particularly to a nasal aspirator capable of effectively preventing backflow and a control method thereof.

2. Description of the Prior Art

A nasal aspirator is a special tool to suck the nasal secretions of a baby because the baby is too small to blow his/her nose by himself/herself. When the nasal secretions are dry to form booger to block the nasal passageway, it is difficult for the baby to breathe.

There are four types of nasal aspirator on the market, namely, a pump-type nasal aspirator, a mouth-suction-type nasal aspirator, a spray-type nasal aspirator and a steam-type nasal aspirator. The pump-type nasal aspirator is easy to use and carry and can suck out nasal mucus and secretions. As to the mouth-suction-type nasal aspirator, the suction can be adjusted by the user, the length of the suction tube is suitable, the small and flexible suction head will not extends into the inside of the nasal cavity, and it is easy to use. The spray-type nasal aspirator and the steam-type nasal aspirator are generally professional medical nasal aspirators. The more high-end nasal aspirator for home use is what we often call an electric nasal aspirator. It is running by "suction", but the energy supply is "electricity".

A conventional electric nasal aspirator mainly relies on a built-in air pump unit to generate suction for extracting the secretions in the nasal cavity into a liquid storage cup of the electric nasal aspirator. In the prior art, due to various reasons such as the overfilling of the liquid storage cup, the liquid is likely to flow back into the air pump unit to cause damage to the air pump unit and to cause inconvenience to the user. An electric nasal aspirator having a liquid detection function to automatically stop an air pump is developed on the market. However, the airway of this electric nasal aspirator is designed too simply and unreasonably. It is triggered too early, resulting in shutdown of the air pump unit. It is inconvenient to use. Therefore, it is necessary to study a solution to solve the above problems.

SUMMARY OF THE INVENTION

In view of the deficiencies of the prior art, the primary object of the present invention is to provide a nasal aspirator capable of effectively preventing backflow and a control method thereof, which can effectively solve the problem that the existing electric nasal aspirator is easy to cause backflow of nasal secretions into the air pump unit or that the air pump unit is easily triggered to cause shutdown.

In order to achieve the above object, the present invention adopts the following technical solutions.

A nasal aspirator comprises a casing, a control board, a lower suction nozzle, an upper suction nozzle, a liquid storage cup, and an air pump unit. The control board is disposed in the casing. The lower suction nozzle is disposed on an upper end of the casing. The lower suction nozzle has a chamber and a suction passageway therein. The chamber has an opening facing upward. An upper end of the suction passageway communicates with the chamber. A detection system for detecting a liquid is provided in the chamber. The detection system is connected to the control board. The upper suction nozzle is mounted to an upper end of the lower suction nozzle. The upper suction nozzle includes a main body shell, an inner tube, and an outer tube. A lower end of the main body shell is hermetically connected to the upper end of the lower suction nozzle. The main body shell has a cavity with an opening facing downward. The cavity communicates with the chamber. The inner tube extends from a top wall of the cavity. The inner tube has a first passageway. The outer tube extends upward from an upper end face of the main body shell. The outer tube has a second passageway. The second passageway communicates with the first passageway. The liquid storage cup is placed in the chamber and the cavity. The liquid storage cup includes a cup body and a cup cover. The cup body has an accommodating chamber with an opening facing upward. The cup cover is disposed on the cup body to cover the opening of the accommodating chamber. The cup cover is formed with a through hole and a mounting hole. The through hole communicates with the accommodating chamber and the cavity. The inner tube passes through the mounting hole and extends into the accommodating chamber. An outer wall of the inner tube is hermetically mated with an inner wall of the mounting hole. The air pump unit is disposed in the casing. An air intake end of the air pump unit communicates with a lower end of the suction passageway. The air pump unit has a motor. The motor is connected to the control board.

A control method of the foregoing nasal aspirator is provided. After the control board is powered on, the air pump unit is turned on and the motor starts to run. The air pump unit generates a suction to suck air in the suction passageway, the chamber, the cavity, the through hole, the accommodating chamber, the first passageway and the second passageway in sequence. When an upper end of the upper suction nozzle is placed in a user's nasal cavity, secretions in the nasal cavity flow through the third passageway, the second passageway and the first passageway in sequence under the action of the suction and flow into the accommodation chamber to be collected. When the motor runs, the control board controls the detection system to detect in real time whether there is a liquid flowing into the chamber of the lower suction nozzle for performing backflow detection. If the liquid is detected, the control board controls the motor to stop funning, or, the motor continues to run for collecting the secretions.

Compared with the prior art, the present invention has obvious advantages and beneficial effects. Specifically, it can be known from the above technical solutions:

By providing the detection system in the cavity, the detection system can detect whether there is a liquid in real time, so as to control the motor of the air pump unit. When the liquid is detected, the motor stops running, which effectively prevents the liquid from backflow to enter the air pump unit. Therefore, the air pump unit is well protected, avoiding damage to the air pump unit and greatly prolonging the service life of the product. The airway of the nasal aspirator is composed of the suction passageway, the chamber, the cavity, the through hole, the accommodating chamber, the first passageway and the second passageway. The airway is designed more reasonably, which effectively avoids shutdown of the air pump unit because the detection system is triggered too early. It is convenient to the use.

DETAILED DESCRIPTION OF THE PREFERRED EMBODIMENTS

Embodiments of the present invention will now be described, by way of example only, with reference to the accompanying drawings.

Figure 1:
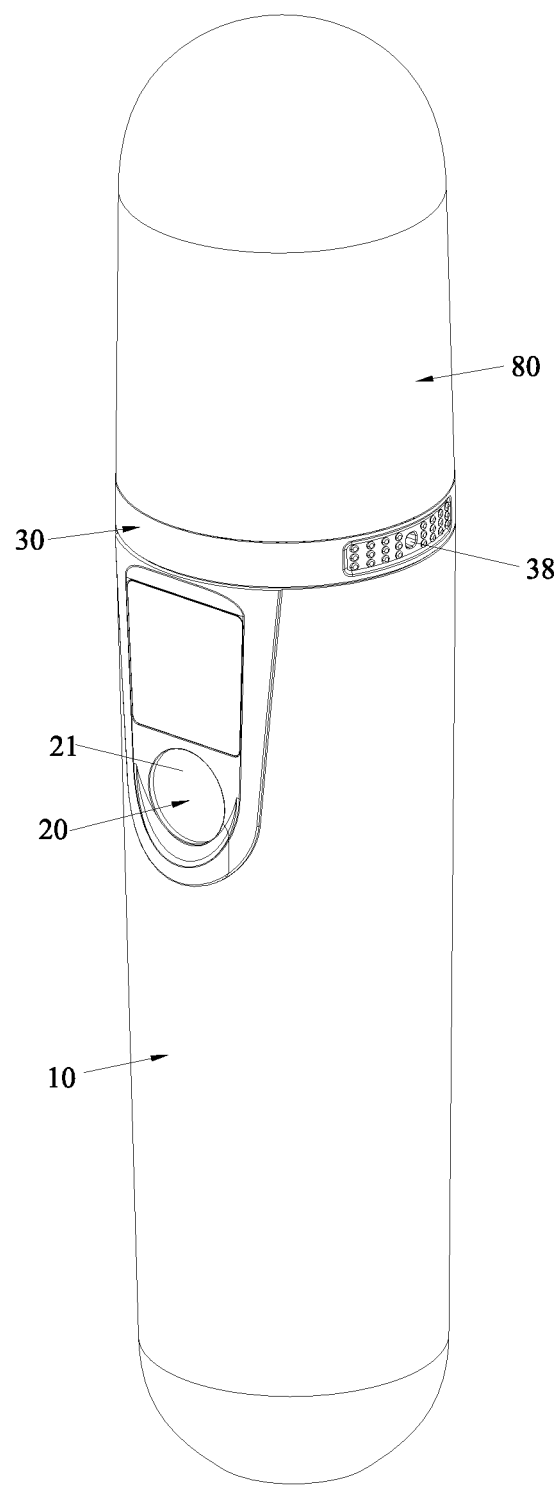
FIG. 1 is a perspective view according to a preferred embodiment of the present invention.
Figure 2:
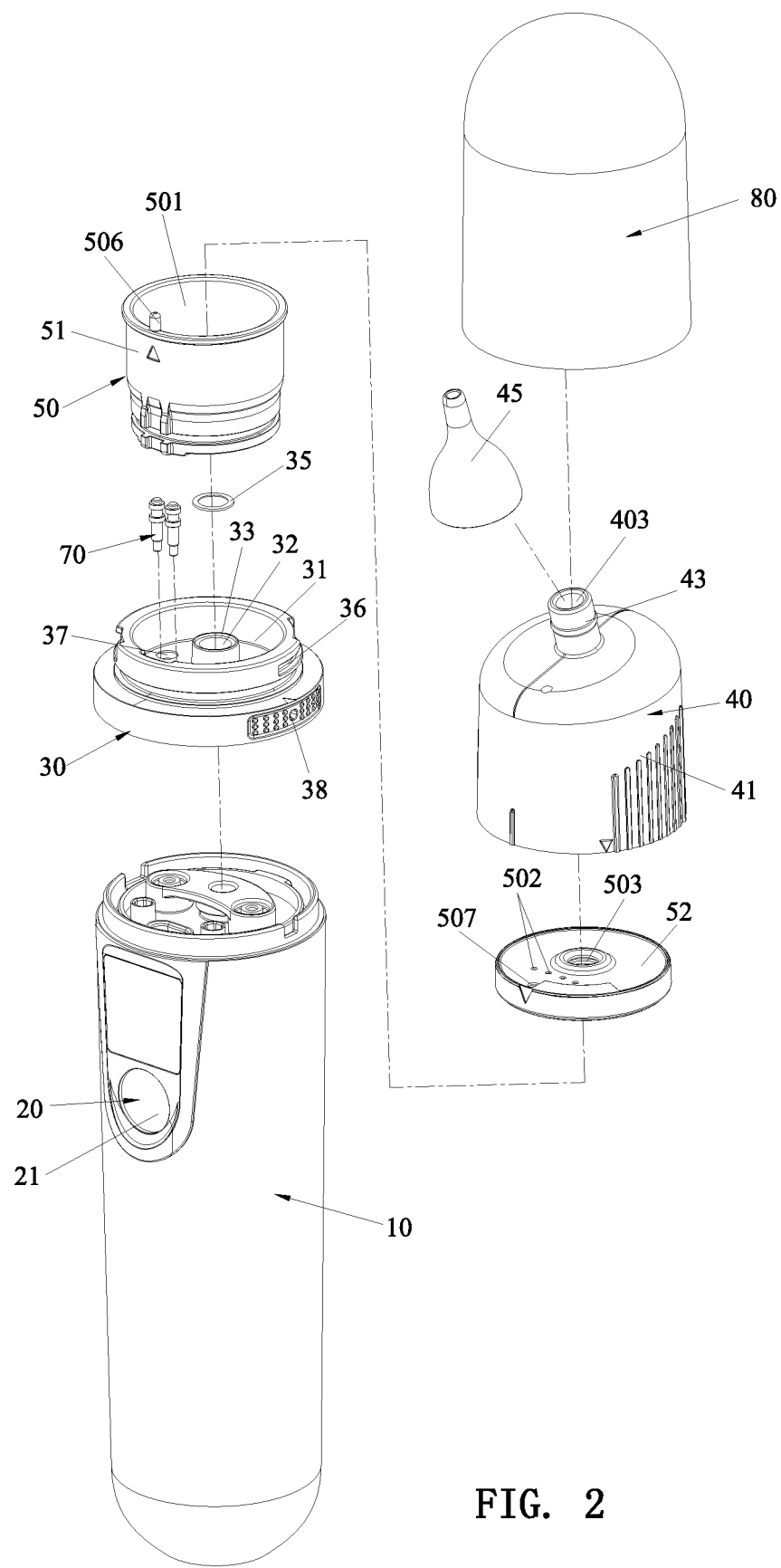
FIG. 2 is an exploded view according to the preferred embodiment of the present invention.
Figure 3:
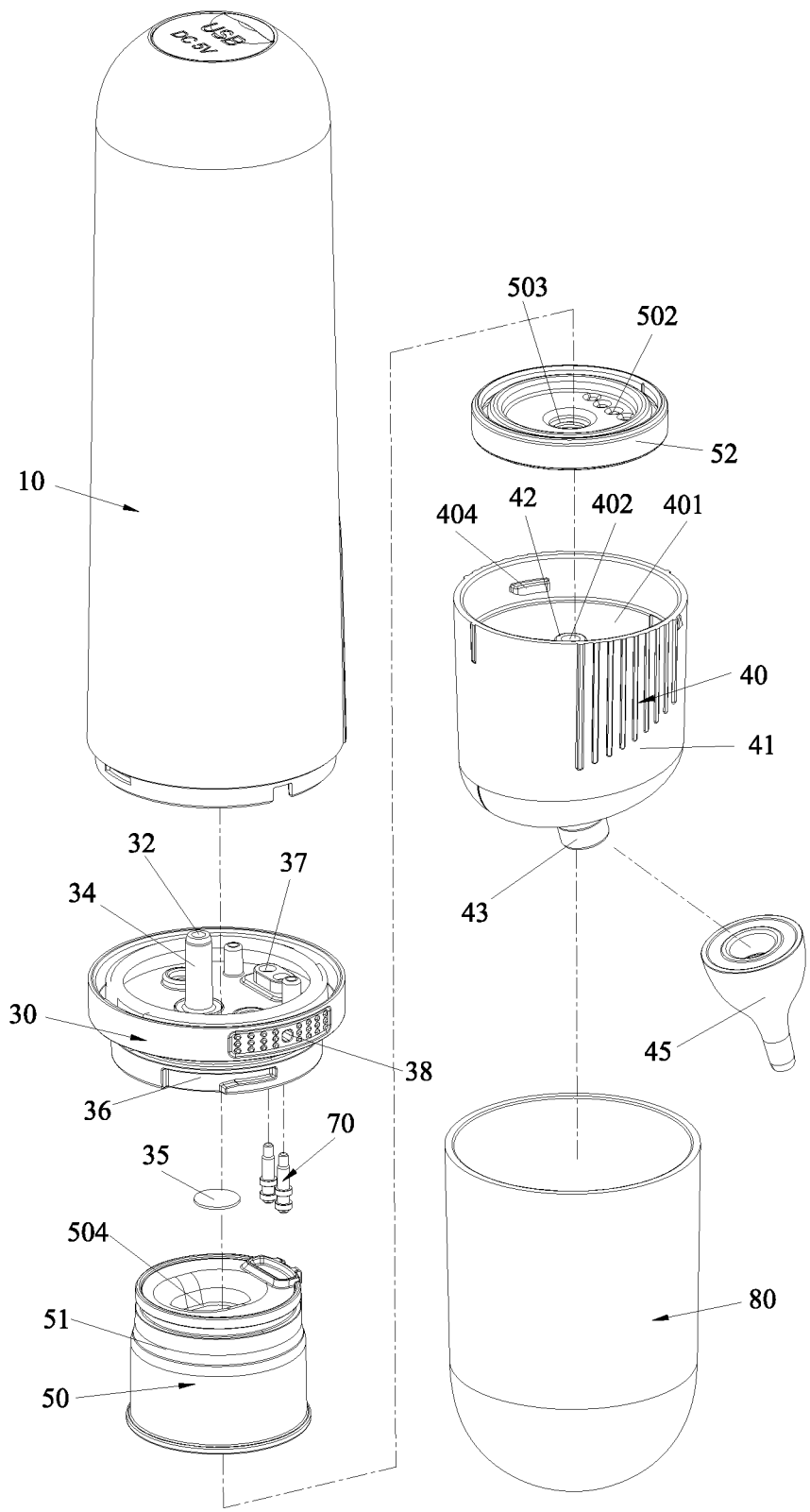
FIG. 3 is another exploded view according to the preferred embodiment of the present invention.
Figure 4:
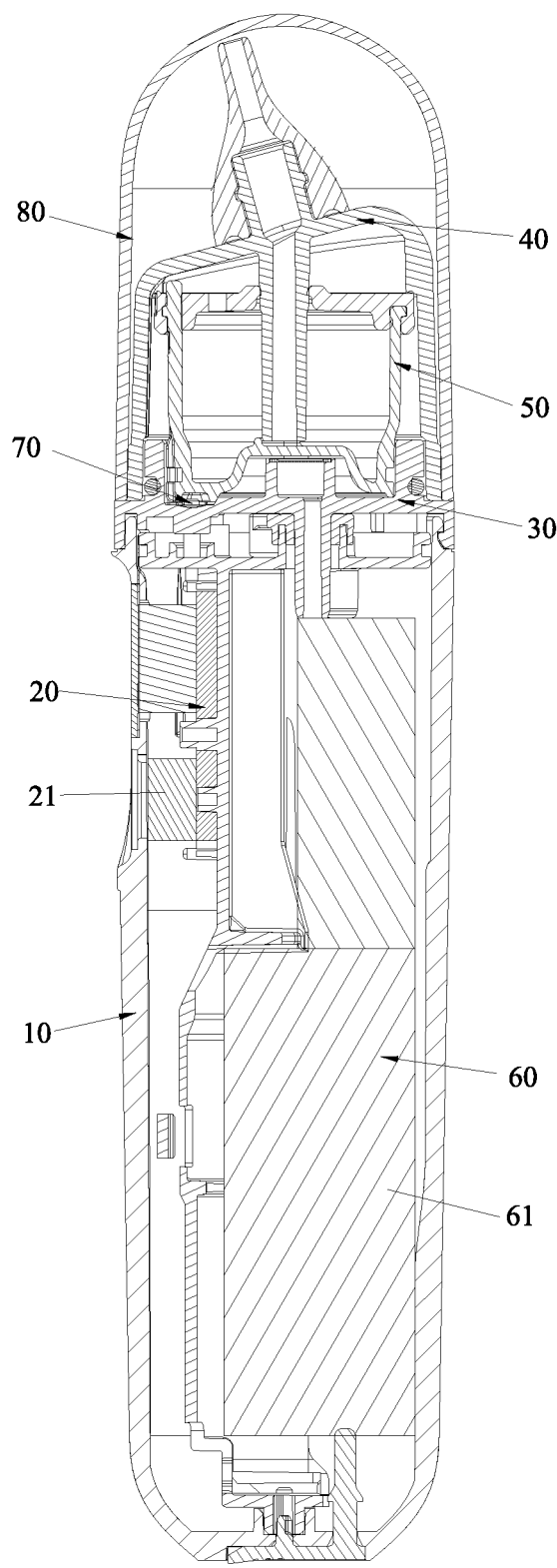
FIG. 4 is a cross-sectional view according to the preferred embodiment of the present invention.
Figure 5:
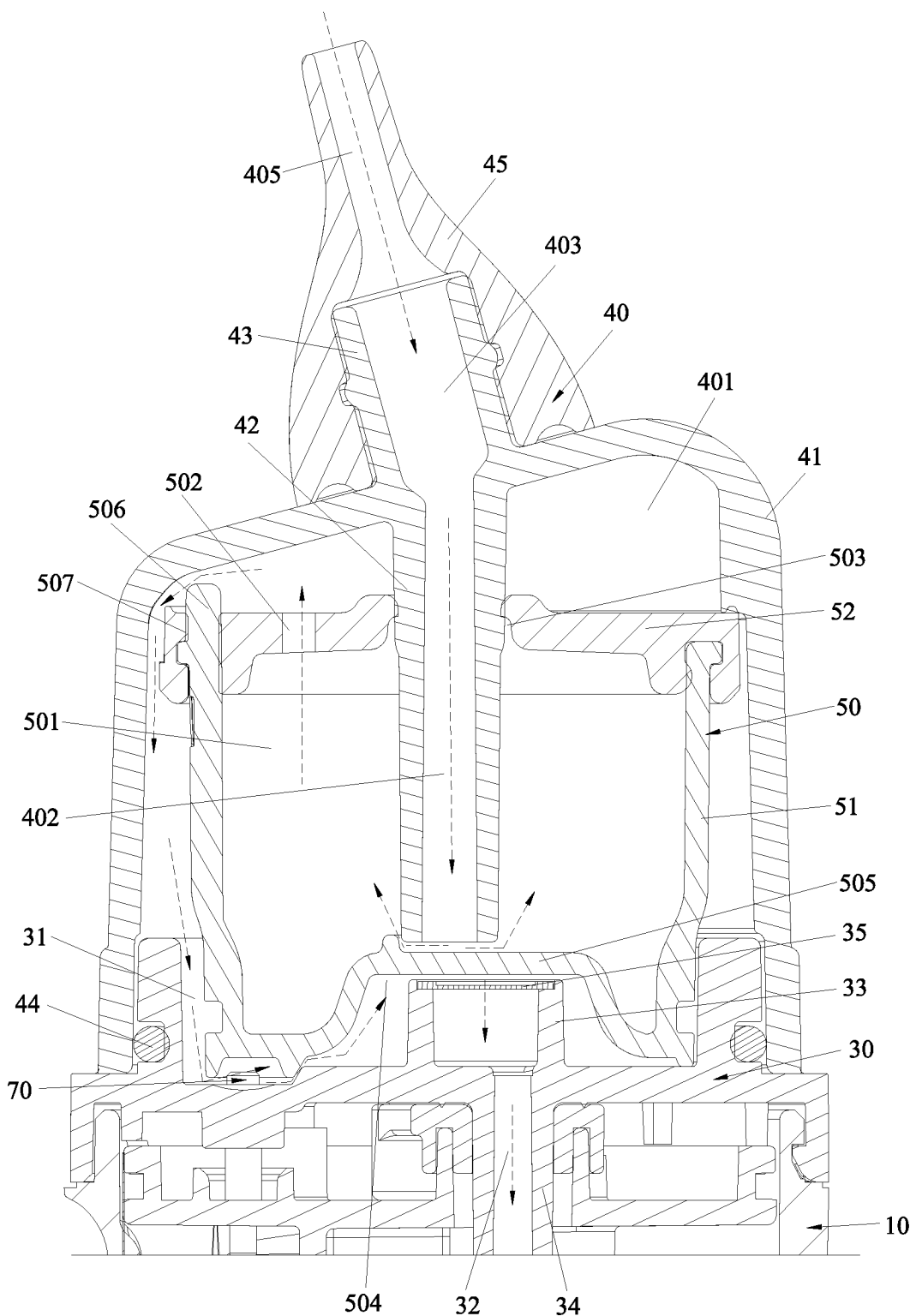
FIG. 5 is a partial cross-sectional view according to the preferred embodiment of the present invention when in use.

Referring to FIG. 1 to FIG. 5, a nasal aspirator capable of effectively preventing backflow according to a preferred embodiment of the present invention comprises a casing 10, a control board 20, a lower suction nozzle 30, an upper suction nozzle 40, a liquid storage cup 50, and an air pump unit 60.

The control board 20 is disposed in the casing 10. The control board 20 has a control button 21. The control button 21 is exposed to the casing 10. The control board 20 may be connected to an external power supply or directly connected to a built-in power supply to supply power to the control board 20.

The lower suction nozzle 30 is disposed on the upper end of the casing 10. The lower suction nozzle 30 has a chamber 31 and a suction passageway 32 therein. The chamber 31 has an opening facing upward. The upper end of the suction passageway 32 communicates with the chamber 31. A detection system 70 for detecting a liquid is provided in the chamber 31. The detection system 70 is connected to the control board 20. In this embodiment, the lower suction nozzle 30 has a first boss 33 extending from the bottom of the chamber 31. The lower suction nozzle 30 further has a connecting tube 34 extending downward from the bottom of the lower suction nozzle 30. The suction passageway 32 is formed in the first boss 33 and the connecting tube 34. A waterproof and breathable membrane 35 is fixed on the upper end face of the first boss 33. The waterproof and breathable membrane 35 covers the upper opening of the suction passageway 32, so as to prevent liquid from flowing into the suction passageway 32 effectively. The outer wall of the upper end of the lower suction nozzle 30 is recessed with an arc-shaped engaging groove 36. The bottom of the chamber 31 is formed with a fixing hole 37. The fixing hole 37 extends downward and passes through the bottom of the lower suction nozzle 30. The detection system 70 is a probe. The probe is inserted and secured in the fixing hole 37. The detection system 70 includes two detection systems 70 connected to the control board 20. The outer wall of the lower suction nozzle 30 is formed with a vent 38 communicating with the inside of the casing 10 for the air pump unit 60 to exhaust air.

The upper suction nozzle 40 is mounted to the upper end of the lower suction nozzle 30. The upper suction nozzle 40 includes a main body shell 41, an inner tube 42, and an outer tube 43. The lower end of the main body shell 41 is hermetically connected to the upper end of the lower suction nozzle 30. The main body shell 41 has a cavity 401 with an opening facing downward. The cavity 401 communicates with the chamber 31. The inner tube 42 extends from the top wall of the cavity 401. The inner tube 42 has a first passageway 402. The outer tube 43 extends upward from the upper end face of the main body shell 41. The outer tube 43 has a second passageway 403. The second passageway 403 communicates with the first passageway 402. In this embodiment, the lower end of the main body shell 41 is sleeved on the upper end of the lower suction nozzle 30. A sealing ring 44 is sandwiched between the inner wall of the lower end of the main body shell 41 and the outer wall of the upper end of the lower suction nozzle 30. An engaging portion 404 extends from the inner wall of the lower end of the main body shell 41. The engaging portion 404 is rotatably engaged with the arc-shaped engaging groove 36. The outer tube 43 is provided with a detachable suction head 45. The suction head 45 has a third passageway 405 therein. The third passageway 405 communicates with the second passageway 403. The upper suction nozzle 40 is provided with a detachable cover 80.

The liquid storage cup 50 is placed in the chamber 31 and the cavity 401. The liquid storage cup 50 includes a cup body 51 and a cup cover 52. The cup body 51 has an accommodating chamber 501 with an opening facing upward. The cup cover 52 is disposed on the cup body 51 to cover the opening of the accommodating chamber 501. The cup cover 52 is formed with a through hole 502 and a mounting hole 503. The through hole 502 communicates with the accommodating chamber 501 and the cavity 401. The through hole 502 includes a plurality of spaced through holes to facilitate air intake. The inner tube 42 passes through the mounting hole 503 and extends into the accommodating chamber 501. The outer wall of the inner tube 42 is hermetically mated with the inner wall of the mounting hole 503. In this embodiment, the outer bottom surface of the cup body 51 has a recess 504. A second boss 505 is formed on the inner bottom surface of the cup body 51. The first boss 33 is located in the recess 504. The inner tube 42 is close to the second boss 505. The lower opening of the first passageway 402 faces the upper surface of the second boss 505. The cup cover 52 is coupled to the cup body 51. A positioning post 506 extends upward from the upper end of the cup body 51. The cup cover 52 has a positioning hole 507. The positioning post 506 is inserted through the positioning hole 507 and extends out of the cup cover 52.

The air pump unit 60 is disposed in the casing 10. The air intake end of the air pump unit 60 communicates with the lower end of the suction passageway 32. The air pump unit 60 has a motor 61. The motor 61 is connected to the control board 20.

The present invention further discloses a control method of the foregoing nasal aspirator capable of effectively preventing backflow. After the control board 20 is powered on, the air pump unit 60 is turned on, and the motor 61 starts to run. The air pump unit 60 generates a suction to suck the air in the suction passageway 32, the chamber 31, the cavity 401, the through hole 502, the accommodating chamber 501, the first passageway 402 and the second passageway 403 in sequence. After the upper end of the upper suction nozzle 40 (i.e. the suction head 45) is placed in a user's nasal cavity, the secretions in the nasal cavity flow through the third passageway 405, the second passageway 403 and the first passageway 402 in sequence under the action of the suction and flow into the accommodation chamber 501 to be collected. When the motor 61 runs, the control board 20 controls the detection system 70 to detect in real time whether there is a liquid flowing into the chamber 31 of the lower suction nozzle 30 for performing backflow detection. If the liquid is detected, the control board 20 controls the motor 61 to stop running, or, the motor 61 continues to run for collecting the secretions.

What is claimed is:

1. A nasal aspirator, comprising a casing, a control board, a lower suction nozzle, an upper suction nozzle, a liquid storage cup and an air pump unit; the control board being disposed in the casing; the lower suction nozzle being disposed on an upper end of the casing, the lower suction nozzle having a chamber and a suction passageway therein, the chamber having an opening facing upward, an upper end of the suction passageway communicating with the chamber, a detection system for detecting a liquid being provided in the chamber, the detection system being connected to the control board; the upper suction nozzle being mounted to an upper end of the lower suction nozzle, the upper suction nozzle including a main body shell, an inner tube and an outer tube, a lower end of the main body shell being hermetically connected to the upper end of the lower suction nozzle, the main body shell having a cavity with an opening facing downward, the cavity communicating with the chamber, the inner tube extending from a top wall of the cavity, the inner tube having a first passageway, the outer tube extending upward from an upper end face of the main body shell, the outer tube having a second passageway, the second passageway communicating with the first passageway; the liquid storage cup being placed in the chamber and the cavity, the liquid storage cup including a cup body and a cup cover, the cup body having an accommodating chamber with an opening facing upward, the cup cover being disposed on the cup body to cover the opening of the accommodating chamber, the cup cover being formed with a through hole and a mounting hole, the through hole communicating with the accommodating chamber and the cavity, the inner tube passing through the mounting hole and extending into the accommodating chamber, an outer wall of the inner tube being hermetically mated with an inner wall of the mounting hole; the air pump unit being disposed in the casing, an air intake end of the air pump unit communicating with a lower end of the suction passageway, the air pump unit having a motor, the motor being connected to the control board; wherein a bottom of the chamber is formed with a fixing hole, the fixing hole extends downward and passes through a bottom of the lower suction nozzle, the detection system is a probe, the probe is inserted and secured in the fixing hole, and the detection system includes two detection systems connected to the control board.

2. The nasal aspirator as claimed in claim 1, wherein the lower end of the main body shell is sleeved on the upper end of the lower suction nozzle, and a sealing ring is sandwiched between an inner wall of the lower end of the main body shell and an outer wall of the upper end of the lower suction nozzle.

3. The nasal aspirator as claimed in claim 1, wherein the lower suction nozzle has a first boss extending from the bottom of the chamber, and the lower suction nozzle further has a connecting tube extending downward from the bottom of the lower suction nozzle, and the suction passageway is formed in the first boss and the connecting tube.

4. The nasal aspirator as claimed in claim 3, wherein a waterproof and breathable membrane is fixed on an upper end face of the first boss, and the waterproof and breathable membrane covers an upper opening of the suction passageway.

5. The nasal aspirator as claimed in claim 3, wherein an outer bottom surface of the cup body has a recess, a second boss is formed on an inner bottom surface of the cup body, and the first boss is located in the recess.

6. The nasal aspirator as claimed in claim 5, wherein the inner tube is close to the second boss, and a lower opening of the first passageway faces an upper surface of the second boss.

7. The nasal aspirator as claimed in claim 3, wherein the cup cover is coupled to the cup body, a positioning post extends upward from an upper end of the cup body, the cup cover has a positioning hole, and the positioning post is inserted through the positioning hole and extends out of the cup cover.

8. The nasal aspirator as claimed in claim 1, wherein the outer tube is provided with a detachable suction head, the suction head has a third passageway therein, the third passageway communicates with the second passageway, and the upper suction nozzle is provided with a detachable cover.

9. A control method of the nasal aspirator as claimed in claim 1, wherein after the control board is powered on, the air pump unit is turned on and the motor starts to run, the air pump unit generates a suction to suck air in the suction passageway, the chamber, the cavity, the through hole, the accommodating chamber, the first passageway and the second passageway in sequence, after an upper end of the upper suction nozzle is placed in a user's nasal cavity, secretions in the nasal cavity flows through a third passageway, the second passageway and the first passageway in sequence under the action of the suction and flows into the accommodating chamber to be collected, when the motor runs, the control board controls the detection system to detect in real time whether there is the liquid flowing into the chamber of the lower suction nozzle for performing backflow detection, if the liquid is detected, the control board controls the motor to stop running, or, the motor continues to run for collecting the secretions.

* * * * *